(12) United States Patent
Li et al.

(10) Patent No.: US 10,234,389 B2
(45) Date of Patent: Mar. 19, 2019

(54) METHOD FOR INSPECTING AN ARTICLE AND APPARATUS FOR MEASURING THE ARTICLE BY MULTI-PHOTON EXCITATION TECHNIQUE

(71) Applicant: CM VISUAL TECHNOLOGY CORPORATION, Tainan (TW)

(72) Inventors: Wang-Yang Li, Tainan (TW); Ming-Che Chan, Taichung (TW); Hsiang-Ning Chen, Yunlin County (TW)

(73) Assignee: CM VISUAL TECHNOLOGY CORPORATION, Tainan (TW)

( * ) Notice: Subject to any disclaimer, the term of this patent is extended or adjusted under 35 U.S.C. 154(b) by 0 days.

(21) Appl. No.: 15/407,354

(22) Filed: Jan. 17, 2017

(65) Prior Publication Data

US 2017/0205347 A1    Jul. 20, 2017

Related U.S. Application Data

(60) Provisional application No. 62/278,995, filed on Jan. 15, 2016.

(51) Int. Cl.
*G01N 21/64* (2006.01)
*G02B 21/00* (2006.01)

(52) U.S. Cl.
CPC ..... *G01N 21/6404* (2013.01); *G01N 21/6458* (2013.01); *G02B 21/0076* (2013.01)

(58) Field of Classification Search
CPC ........... G02B 21/0076; G01N 21/6404; G01N 21/6458

USPC ......................................................... 250/340
See application file for complete search history.

(56) References Cited

U.S. PATENT DOCUMENTS

| | | | | |
|---|---|---|---|---|
| 5,523,573 | A * | 6/1996 | Hanninen | G01N 21/6408 250/459.1 |
| 6,469,794 | B1 * | 10/2002 | Piltch | G01N 21/6408 356/601 |
| 7,118,845 | B2 * | 10/2006 | DeVoe | C08F 2/50 430/270.1 |
| 8,441,633 | B2 | 5/2013 | Truong et al. | |
| 2003/0004306 | A1 * | 1/2003 | Miyawaki | C07K 14/43595 530/300 |
| 2004/0178356 | A1 * | 9/2004 | Natori | G02B 21/0032 250/458.1 |
| 2005/0259319 | A1 * | 11/2005 | Brooker | G02B 21/0076 359/368 |

(Continued)

OTHER PUBLICATIONS

TIPO Office Action dated Jul. 25, 2017 in Taiwan application (No. 105140641).

*Primary Examiner* — Taeho Jo (74) *Attorney, Agent, or Firm* — McClure, Qualey & Rodack, LLP (57) ABSTRACT

A method for inspecting an article containing a target material is provided. A sampling position of the article is illuminated by a beam of laser light having a wavelength $\lambda$. Illumination focus to a focal point at the sampling position of the article to produce molecular excitation of the target material by simultaneous absorption of n incident photons of the beam of laser light, wherein n is equal to or greater than two. An output light exited from the article is analyzed by a detector, wherein the output light is of a wavelength range between $0.8\lambda$ and $1.2\lambda$.

20 Claims, 7 Drawing Sheets

(56) References Cited

U.S. PATENT DOCUMENTS

| | | | | |
|---|---|---|---|---|
| 2006/0017452 | A1* | 1/2006 | Yamamoto | G01R 31/2812 324/750.3 |
| 2007/0091307 | A1* | 4/2007 | Brooker | G02B 21/0076 356/318 |
| 2008/0044148 | A1* | 2/2008 | Robinson | B82Y 20/00 385/122 |
| 2008/0092310 | A1* | 4/2008 | Miki | B22F 1/0022 8/524 |
| 2008/0116392 | A1* | 5/2008 | Brooker | G02B 21/0076 250/458.1 |
| 2008/0174766 | A1* | 7/2008 | Haaslahti | G01N 21/6408 356/73 |
| 2009/0075014 | A1* | 3/2009 | Miki | B82Y 10/00 428/64.4 |
| 2010/0055448 | A1* | 3/2010 | Tomura | B82Y 10/00 428/328 |
| 2010/0188496 | A1* | 7/2010 | Xie | G01J 3/10 348/79 |
| 2010/0261263 | A1* | 10/2010 | Vo-Dinh | A61L 2/08 435/287.1 |
| 2011/0122488 | A1* | 5/2011 | Truong | G01N 21/6408 359/385 |
| 2011/0147613 | A1* | 6/2011 | Rigneault | G01N 21/6458 250/458.1 |
| 2011/0240617 | A1* | 10/2011 | Xu | B23K 26/00 219/121.72 |
| 2012/0098164 | A1* | 4/2012 | Kan | B29C 64/135 264/494 |
| 2012/0126226 | A1* | 5/2012 | Kuwabara | H01L 21/288 257/43 |
| 2012/0228802 | A1* | 9/2012 | Kan | B29C 64/135 264/401 |
| 2014/0283873 | A1* | 9/2014 | LeClaire | B08B 7/0042 134/1.3 |
| 2014/0300890 | A1* | 10/2014 | Lange | G01N 21/9501 356/51 |
| 2014/0356969 | A1* | 12/2014 | Nishikawa | G02B 21/00 436/94 |
| 2015/0008340 | A1* | 1/2015 | Fujita | G02B 21/0076 250/459.1 |
| 2015/0069268 | A1* | 3/2015 | Schoenborn | A61B 5/0059 250/459.1 |
| 2015/0218628 | A1* | 8/2015 | Hanashi | G01N 21/76 506/9 |
| 2015/0308814 | A1* | 10/2015 | Li | G01B 11/0658 250/458.1 |
| 2015/0338345 | A1* | 11/2015 | Lakowicz | G01N 33/58 435/5 |
| 2016/0054496 | A1* | 2/2016 | Ichihashi | G01N 21/88 250/338.1 |
| 2016/0123812 | A1* | 5/2016 | Kyogaku | G01N 21/65 356/301 |
| 2016/0178439 | A1* | 6/2016 | Freudiger | G01J 3/44 356/301 |
| 2017/0146458 | A1* | 5/2017 | Huber | G01J 3/10 |

* cited by examiner

METHOD FOR INSPECTING AN ARTICLE AND APPARATUS FOR MEASURING THE ARTICLE BY MULTI-PHOTON EXCITATION TECHNIQUE

This application claims the benefit of U.S. Provisional Application No. 62/278,995, filed Jan. 15, 2016, the subject matter of which is incorporated herein by references.

BACKGROUND

Technical Field

The disclosure relates in general to a method for inspecting an article and an apparatus for measuring the same, and more particularly to a method for detecting an article by a multi-photon excitation technique and an apparatus of modified multi-photon fluorescence microscope for measuring the article.

Description of the Related Art

By doping various active materials within substrates or the matrix, various optical functions, including optical amplification, absorption, wavelength filtering, solid-state lighting and polarization distinction, can thus be performed. The followings are some examples. First, the laser crystal, formed by active-ion-doping into a bulk crystal, is the key element for optical amplification. For example, the Ti:Sapphire laser crystal is a sapphire ($Al_2O_3$) crystal doped with titanium ions. Second, for optical absorption and wavelength filtering, the absorptive filters or colored glass filters can be used, which are usually made from glass or plastics in which many absorptive active-ions have been added. These active ions transmit some wavelength components of light while attenuating others with extremely high absorption constants. For many filtering problems, these ion-doped wavelength filters are better choices than interference-type filters due to their much better wavelength extinction ratio. Third, in white organic light-emitting diodes (OLEDs), the low-gap dopants are dispersed deep inside the emissive layer. Through electrical pumping, visible wavelength components are radiated in the emissive layer. Finally, for the fabrication of polarizing plates which are key elements in liquid crystal displays, iodine-dyed ions added in the polyvinyl alcohol (PVA) polymer film(s) function as polarization-dependent light absorbers.

It is essential to monitor the spatial distribution and uniformity of dopants in the substrates or the matrix, such as laser crystals, color-glass filters, white OLEDs and polarizers mentioned above. The doped condition of the laser crystal is strongly related to the laser performance, including the threshold pumping power, slope efficiency and output power. When low-gap dopants are not uniformly dispersed in the emissive layer of OLED devices, this can lead to spatial variation in the color of the white electroluminescence, affecting lighting applications. The spatial distribution of doped iodine ions in PVA polymer films would be helpful for extracting and mapping more properties of a polarizer.

According to an analysis method of dopant spatial distributions or concentrations within the matrix known in the art requires a biopsy, including the removal (such as slicing), fixation, and staining of a piece sample from the object under test. The sliced samples are then put under a microscope to measure and analyze the image to show the relative concentrations of dopants. However, conventional analysis of dopant distribution or uniformity involves many time-consuming and complicated steps, for example, sample preparation and treatment and analysis steps. Also, the conventional slicing procedures are invasive, destructive, and time-consuming, such that the relative ion concentrations cannot be monitored quickly and in real time during fabrication process with high accuracy. Therefore, it would be desired for the researches to develop devices and methods for analysis of dopant distribution more simple and time-saving. Particularly, it is highly desired to develop a fast and biopsy-free method for analyzing a target material in the articles to be tested; for example, for quickly and accurately analyzing the doped ion concentration in an optical substrate (ex: a PVA film of a polarizer).

Two-photon fluorescence (TPF) microscope has been widely utilized in biological, chemical, and clinical applications. TPF processes usually involve fluorescent molecules with third-order nonlinearity, where two-excitation photons with equal energies are simultaneously absorbed by fluorescent molecules through the two-photon absorption (TPA) effect and one emission photon with a higher energy is generated. Molecular concentration imaging can thus be performed by measuring the intensities of higher-energy fluorescence photons, with a natural depth discrimination capability and high spatial resolutions in the focal plane. However, TPF microscope is not always suitable for monitoring the molecular concentration due to the non-radiative processes (i.e. non-fluorescent processes) that occur in some doped-ions or molecules when they are excited by TPA effects. Accordingly, for the doped-ions or molecules tending to occur the non-radiative processes, the doped-ions concentration would not be accurately determined by the conventional TPF microscopy.

SUMMARY

The disclosure is directed to a method for inspecting an article and an apparatus for measuring the article by a multi-photon excitation technique. This embodied method and apparatus have great potential for monitoring the spatial distributions of a target material in the article quickly and non-destructively, which would be of great benefit in both scientific research and industrial applications.

According to the disclosure, a method for inspecting an article is provided, comprising providing the article containing a target material; illuminating a sampling position of said article by a beam of laser light having a wavelength $\lambda$; focusing said illumination to a focal point at a sampling position of the article to produce molecular excitation of the target material by simultaneous absorption of n incident photons of the beam of laser light, wherein n is equal to or greater than two; and analyzing an output light exiting from the article by a detector, wherein the output light is of a wavelength range between $0.8\lambda$ and $1.2\lambda$.

According to the disclosure, an apparatus for measuring an article by a multi-photon excitation technique, at least comprising stage means for receiving an article containing a target material; at least one source of coherent pulsed light having a wavelength $\lambda$; lens means for focusing said coherent pulsed light to an object plane within the article at a sampling position, thereby causing said target material to simultaneously absorb n photons of the coherent pulsed light, wherein n is equal to or greater than two; and detector for detecting a light intensity of an output light exiting from the article, wherein the output light is of a wavelength range between $0.8\lambda$ and $1.2\lambda$.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

DETAILED DESCRIPTION

The embodiments are provided hereinafter with reference to the accompanying drawings for describing the related procedures of the inspecting method and the configuration of the apparatus of modified multi-photon fluorescence microscope, but the present disclosure is not limited thereto. It is noted that not all embodiments of the invention are shown. Modifications and variations can be made without departing from the spirit of the disclosure to meet the requirements of the practical applications. Thus, there may be other embodiments of the present disclosure which are not specifically illustrated. It is also important to point out that the illustrations may not be necessarily drawn to scale. Thus, the specification and the drawings are to be regard as an illustrative sense rather than a restrictive sense.

In the present disclosure, a non-invasive method for analyzing a target material within an article by a multi-photon excitation technique and an apparatus for performing the same are disclosed. In the present disclosure, a method for inspecting an optical matter and an apparatus of modified multi-photon fluorescence microscope for performing the inspection are disclosed. More specifically, an embodiment of the present disclosure provides an optical sectioning diagnosis method to determine the presence of a particular substance in a sample and, in many cases, to quantify the amount of the substance or to depict a distribution profile of a target material along the detection trace within a sample by two-photon excitation technique, and an apparatus for performing the same is also provided in the embodiment. The embodied method is a quick and reliable way for analyzing a target material (ex: relative ion concentrations or depth-concentration profile) of the optical matter in real time during fabrication process with high accuracy, thereby improving the properties of the optical matter in time and accurately. Accordingly, the performance of the device applied with the improved optical matter would be reliable and satisfy the device requirements during the operation.

The disclosure can be applied to various applications with to-be-detected articles such as optical matters, especially for the optical matters having materials occurring non-radiative processes during multi-photon absorption. In the embodiment, an optical substrate containing doped ions, such as a polarizer containing iodine-dyed PVA polymer films, is exemplified for illustration. It is noted that the present disclosure is not limited to the polarizer application. Also, in the embodiment, a modified two-photon fluorescence (m-TPF) microscope is utilized to trace the doped-ion concentrations deep inside transparent optical substrates. However, other multi-photon fluorescence (MPF) microscopy, such as three-photon fluorescence microscope (or more) can be modified and utilized in the application. The disclosure is not limited to the m-TPF microscope for analyzing the to-be-detected articles.

The detecting method of the embodiment is completely different from the fluorescence measurement of the emission photon in the typical two-photon fluorescence microscopy. In the detecting method of the disclosure, the pulsed light source is provided for illuminating an article containing a target material, thereby producing molecular excitation of the target material by simultaneous absorption of multiple incident photons of the beam of laser light. A multi-photon absorption (MPA) effect caused by the target material in the article can be quickly obtained by comparing the attenuation of the light-transmitted from the article with the incident. Thus, the existence of the target material in the article can be quickly determined according to the multi-photon absorption effect. According to the embodiment, the pulsed laser is provided for focusing to the article, wherein simultaneous absorption of n incident photons of laser light occurs at the target material. Then, a light density of an output light exited from the article is analyzed for determining the change of multi-photon absorption (MPA) effect, wherein the output light is of a wavelength around the incident light wavelength $\lambda$ (such as a wavelength in a range of $0.8\lambda$ to $1.2\lambda$), which is longer than the wavelength of multi-photon fluorescence (MPF) effect. Consequently, the relative concentration or the concentration distribution of the target material along the detection trace in the article can be obtained. Take two-photon absorption (TPA) for illustration, the TPA effect is proportional to the localized ion concentrations within a small volume near the focal plane, and can be directly detected by measuring the intensity loss of the pumped incident photons. In the embodiments, iodine-dyed PVA polymer films of the polarizer are exemplified for demonstration purposes. By simply changing the relative position of the polarizer and the focusing objective in the m-TPF microscope (ex: scanning along the z-direction, which is vertical to the polarizer extended in the xy-plane), the axial distribution (ex: z-direction) of the doped ions (i.e. Iodine-dyed ions), utilized to distinguish the durability of a polarizer, can be quickly and accurately measured in a non-invasive manner. Moreover, two-dimensional (2D) biopsy images of the relative ion concentrations (i.e. a virtual image of a combination of the MPA effect results detected at different focal planes) comparable to traditional microscopic images of sliced samples, can also be obtained without any physical biopsy. These demonstrated results show that the m-TPF of the embodiment has great potential for monitoring the spatial distributions of doped-ions inside the optical matter (such as optical substrate) quickly and non-destructively, which will be of benefit in both scientific research and industrial applications.

The working principles are further described below. Modified multi-photon fluorescence (m-MPF) microscope (such as two, three, or more photons) can be applied in the disclosure, and the working principles of two-photon fluorescence microscope and multi-photon fluorescence microscope are described below. Please refer to FIG. 1A, FIG. 1B and FIG. 1C.

Figure 1A:
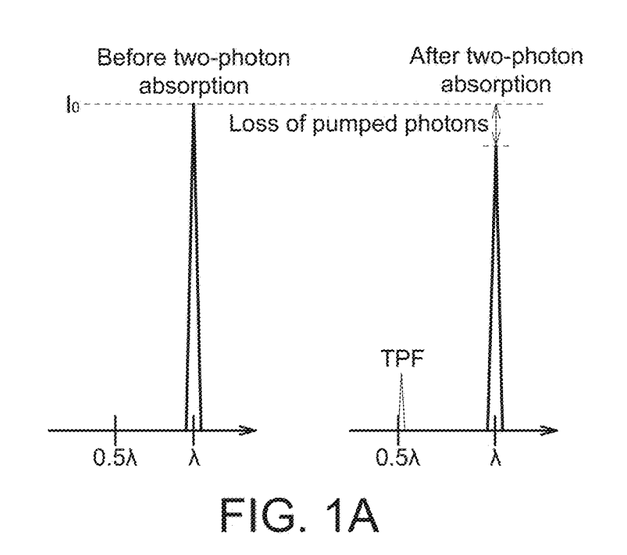
FIG. 1A illustrates the working principles and design of a modified two-photon fluorescence microscope by the input/output spectra according to the embodiment of the disclosure.

FIG. 1A illustrates the working principles and design of a modified two-photon fluorescence microscope by the input/output spectra according to an embodiment of the disclosure. The input spectra of the pumped incident photons having a wavelength λ and intensity of $I_0$ is shown in the left hand of FIG. 1A (before two-photon absorption). By the two-photon absorption process from the localized dopant deep inside an optical matter such as a transparent substrate, the output spectra of femtosecond laser and two-photon fluorescence are shown in the right hand of FIG. 1A (after two-photon absorption). In some conditions, instead of two-photon absorption, non-radiative processes dominate after the two-photon absorption of a pair of lower energy photons. Moreover, two-photon absorption signals with higher photon energies could be re-absorbed or may not penetrate the substrates. Due to these two reasons, in this embodiment, localized ion concentrations are monitored through the intensity loss of the pumped incident photons at the specified wavelength (i.e. wavelength λ). Accordingly, the intensity loss of the pumped incident photons is monitored for mapping and determining the doped-ion (i.e. target material) concentration of the optical matter.

Figure 1B:
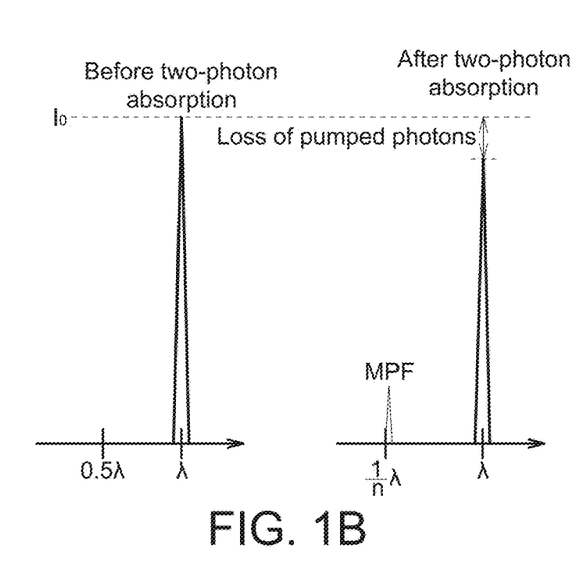
FIG. 1B illustrates the working principles and design of a modified multi-photon fluorescence microscope by the input/output spectra according to another embodiment of the disclosure.

FIG. 1B illustrates the working principles and design of a modified multi-photon fluorescence microscope by the input/output spectra according to another embodiment of the disclosure. Similar to the working principles of the two-photon fluorescence microscope as described above, the input spectra of the pumped incident photons having a wavelength λ and intensity of $I_0$ is shown in the left hand of FIG. 1B (before n-photon absorption), and an output spectra of femtosecond laser and multi-photon fluorescence (MPF) by the multi-photon absorption (MPA) are shown in the right hand of FIG. 1B (after n-photon absorption). In FIG. 1B, "n" means n-photon absorption; for example, n is equal to three if a modified three-photon fluorescence microscope is utilized in the disclosure. Similarly, the localized ion concentrations in the article are monitored through the intensity loss of the pumped incident photons at the specified wavelength (i.e. wavelength λ).

Figure 1C:
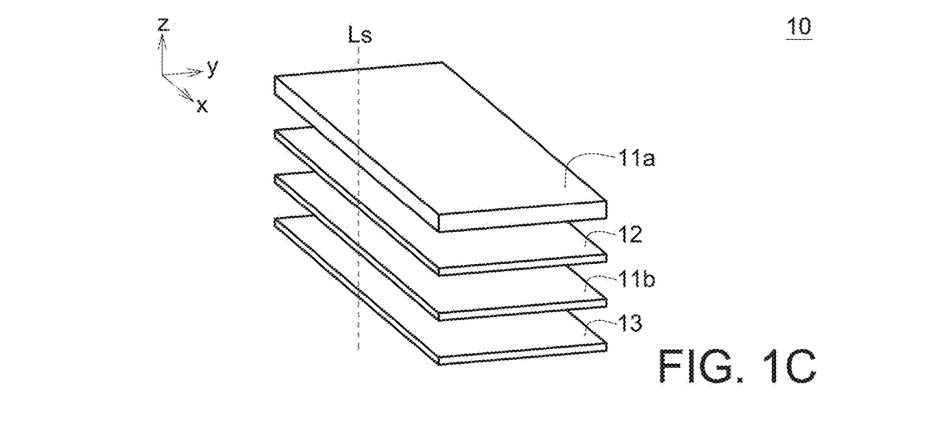
FIG. 1C depicts a layered structure of a polarizer.

FIG. 1C depicts an embodiment of a layered structure of a polarizer. As shown in FIG. 1C, the polarizer 10 may include a tri-acetyl cellulose (TAC) film 11a with surface treatment, a uniaxial poly vinyl alcohol (PVA) layer 12, a TAC film 11b as a wide viewing compensation layer, and a pressure sensitive adhesive (PSA) layer 13, from the surface of the polarizer to the LCD cell. These functional layers compose a complex multi-layered polarizer 10. Except for the thick uni-axially PVA layer (ex: 25 μm), all other layers are highly transparent to visible and Near-infrared (NIR) light. The dashed line Ls represents a scanning trace by a modified multi-photon fluorescence microscope, and the scanning trace is extended along the z-direction (i.e. vertical to the xy-plane).

Figure 2A:
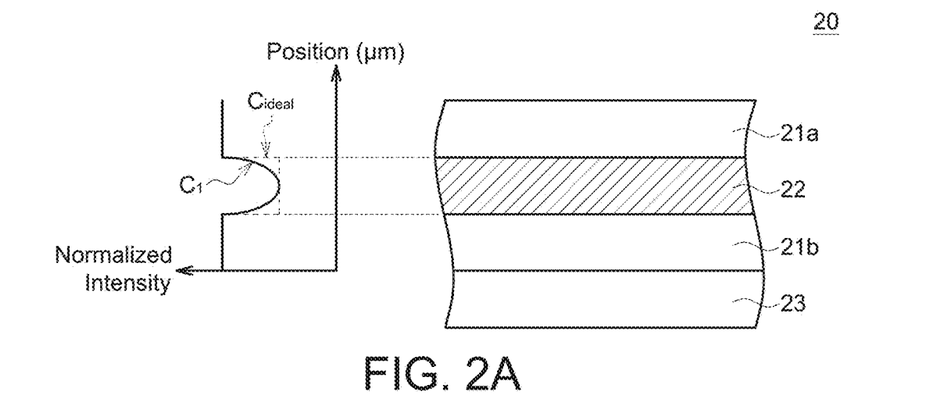
FIG. 2A and FIG. 2B illustrate the durable and poorly-durable polarizers and the corresponding concentration distribution of the target material in the polarizers, respectively.
Figure 2B:
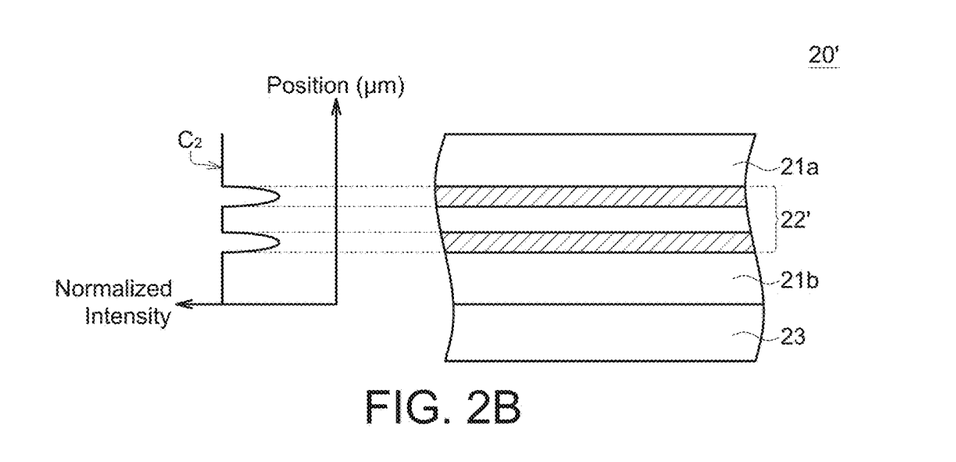

According to the experiments conducted in the embodiment, two types of polarizers, durable and poorly-durable, are tested. Please refer to FIG. 2A and FIG. 2B, which respectively illustrate the durable and poorly-durable polarizers and the corresponding concentration distribution of the target material in the polarizers. The polarizer 20/20' comprises the PVA layer 22/22' sandwiched between the TAC layers 21a and 22b, and the PSA layer 23 is formed on the TAC layer 21b. As shown in FIG. 2A, in the durable polarizer 20 (ex: with excellent durability), the iodine-dyed ions are spread uniformly throughout the entire PVA layer 22 deep within the polarizer 20 (i.e. the slash mark portion in FIG. 2A); thus, the polarization extinction ratio can last for a long time. In FIG. 2A, the corresponding concentration distribution of the iodine-dyed ions in the durable polarizer is represented by an experimental curve $C_1$, which shows a single lower point of the intensity (i.e. an intensity loss peak of the pumped incident photons at the wavelength λ). The experimental curve $C_1$ is close to but not completely identical to the ideal curve $C_{ideal}$ due to the limitation of axial resolution (for example, z-direction resolution in this embodiment) of the multi-photon microscope. As shown in FIG. 2B, in the poorly-durable polarizer, the iodine-dyed ions are clustered near both interfaces between the PVA layer 22' and the TAC layer 21a/21b (i.e. the slash mark portion in FIG. 2B). The clustered iodine-dyed ions can easily diffuse to the TAC layer 21a/21b over time, which leads to degradation of the corresponding polarization distinguishing capabilities with the diffusion, thereby causing considerable effect on the optical performance of liquid-crystal displays in the application. In FIG. 2B, the corresponding concentration distribution of the iodine-dyed ions in the poor durable polarizer 20' is represented by an experimental curve $C_2$, which shows two lower points of the intensity (i.e. two intensity loss peaks of the pumped incident photons at the wavelength λ) corresponding to the positions of iodine-dyed ions near both interfaces between the PVA layer 22' and the TAC layer 21a/21b. Results in FIG. 2A and FIG. 2B show that the multi-photon absorption of the embodiment has great potential for quickly and non-destructively monitoring the spatial distributions of doped-ions (such as iodine-dyed ions) inside the article such as an optical matter (ex: the polarizer as exemplified herein).

Figure 3:
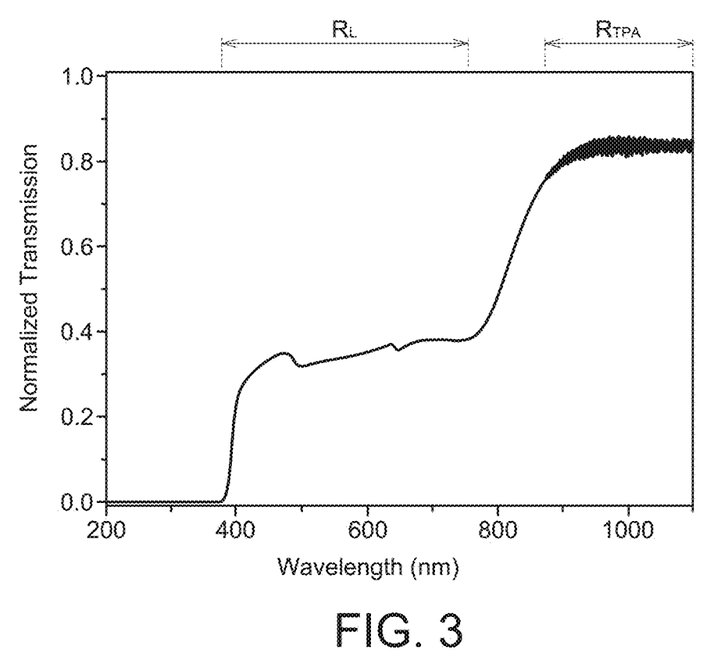
FIG. 3 shows a measured transmission spectrum of polarizer.

The wavelength selection is further described below. The wavelength selection for the modified multi-photon fluorescence microscope of the embodiment is important because it is related to the spatial resolution and depth sectioning capability. Excitation with shorter wavelengths contributes to a better spatial resolution in three dimensions. However, if the excitation wavelength is too short, instead of the MPA effect, the linear absorption effect will occur, which will destroy the natural depth discrimination capability. Thus, before performing the modified multi-photon fluorescence microscope of the embodiment, the transmission spectrum of the sample was first measured. Take a modified two-photon fluorescence microscope for example, the transmission spectrum of the sample was first measured, and the measurement result is shown in FIG. 3. From the measured spectrum, as shown in FIG. 3, the transmission efficiency is within the 30% to 40% range in the visible wavelength (about 400 nm to about 780 nm) region. It is derived from the fact that most photons in one polarization are linearly absorbed by the PVA layer of the polarizer (absorption axis) and other photons with perpendicular polarization are transmitted (transmission axis). In the wavelength beyond about 900 nm, the transmission efficiencies of the whole polarizer increased to ~80%. FIG. 3 also indicates that when the wavelength is shorter than 780 nm, the polarizer is highly absorptive, which corresponds to the linear absorption region $R_L$ (one-photon absorption region). On the other hand, the polarizer is relatively transparent in regions where the wavelength is longer than about 900 nm. When excited by a focused femtosecond laser beam with an output wavelength beyond about 900 nm, the one-photon absorption effect was suppressed and the TPA effect only occurred near the focal point, wherein the output wavelength beyond about 900 nm corresponds to the two-photon absorption region $R_{TPA}$. Thus, FIG. 3 indicates that the wavelength region (i.e. $R_L$) ranged from 400 nm-800 nm is for one-photon absorption of Iodine-dyed layer in the PVA film, and the wavelength region beyond 900 nm is suitable for two-photon absorption (i.e. $R_{TPA}$). Accordingly, in one embodiment, the wavelength λ of the pump beam of laser light for the m-TPF microscope of the embodiment is longer than about 900 nm. In another embodiment, the beam of laser light has a wavelength λ in a range of longer than about 900 nm and shorter than about 1600 nm. In another embodiment, the beam of laser light has a wavelength λ in a range of longer than about 900 nm and shorter than about 1200 nm; for example (but not limited), about 1030 nm (central wavelength) in one application.

Accordingly, if a modified multi-photon fluorescence microscope is applied in the embodiment, the wavelength selection for the modified multi-photon fluorescence microscope depends on the wavelength of photon absorption region for the target material. For example, if it is measured that the wavelength of one-photon absorption region for the target material is a region from λ1 to λ2 (ex: 400 nm to 800 nm), the wavelength of two-photon absorption (TPA) region will be a region from 2×λ1 to 2×λ2 (ex: 800 nm to 1600 nm), the wavelength of three-photon absorption region will be a region from 3×λ1 to 3×λ2 (ex: 1200 nm to 2400 nm), and the wavelength of multi(n)-photon absorption region will be a region from n×λ1 to n×λ2. Additionally, the pulsed light sources (such as a laser source) for absorption of different photons, such as the pulsed light sources of two-photon absorption and three-photon absorption, have different wavelengths, different output pulse durations or pulse energies depend on the intended purposes. For example, the output pulse durations of a laser source adopted in a modified two-photon fluorescence microscope is 250 fs, and the value of the output pulse durations of the laser source adopted in a modified three-photon fluorescence microscope would be lower.

Figure 4:
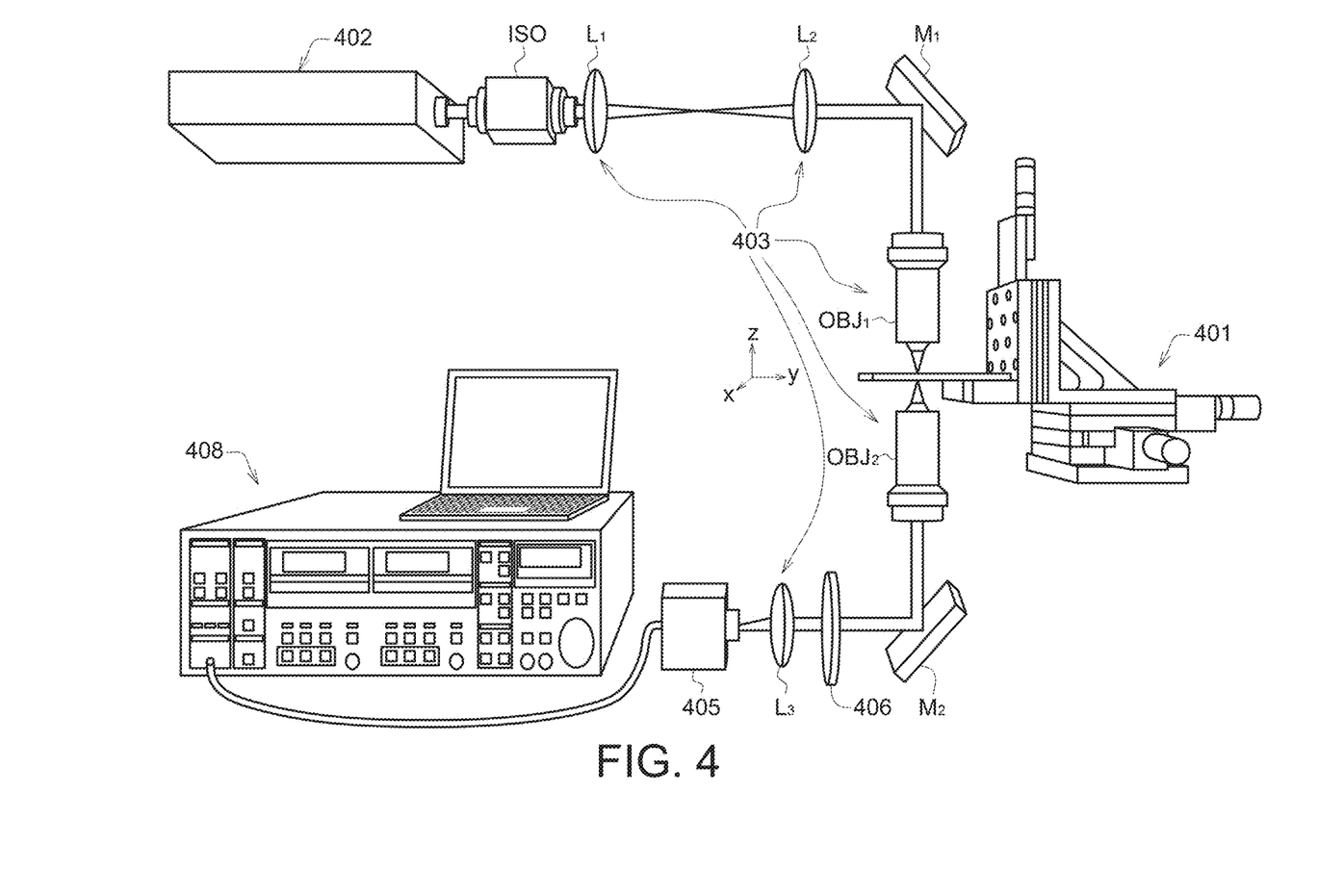
FIG. 4 shows an outline of an apparatus of modified multi-photon fluorescence microscope according to the embodiment.

FIG. 4 shows an outline of an apparatus of modified multi-photon fluorescence microscope according to the embodiment. However, the configuration of FIG. 4 is used for demonstrating, not for limiting the modified multi-photon fluorescence (MPF) microscope of the embodiment, and the details could be adjusted or slightly changed. An apparatus of modified multi-photon fluorescence microscope, at least comprises stage means 401; at least one source 402 (such as a laser source) of coherent pulsed light, and the source 402 having an isolator ISO; lens means 403 such as the lens $L_1$, $L_2$, $L_3$ and the focusing and collimating objectives $OBJ_1$ and $OBJ_2$; and the detector 405. According to the embodiment, the source 402 illuminates a sampling position of the target material of the article by the coherent pulsed light (ex: laser) having a wavelength λ. The lens means 403 focuses the coherent pulsed light on a focal point, the focal point of the coherent pulsed light is located on the object plane in the target material of the article, thereby causing the target material to simultaneously absorb at least two or more photons and produce fluorescence photons. Different from the measurement of the typical multi-photon fluorescence microscopy, an output light exited from the article is analyzed by a detector 405, wherein the analyzed output light is of a wavelength range between 0.8λ and 1.2λ. For example, the analyzed light is of a wavelength range around the incident light wavelength λ. In one embodiment, the analyzed output light is of a wavelength range between 0.9λ and 1.1λ. In one embodiment, the detector 405 detects an output light intensity substantially at the wavelength λ after the pulsed light exits from the article (ex: polarizer), so as to obtain an intensity loss of the pumped incident photons of the wavelength λ (please also refer to FIG. 1A and FIG. 1B).

Also, the apparatus of multi-photon fluorescence microscope of the embodiment may further include a filter means 406, such as one or more of color glass filters (CGF) for filtering out light having wavelengths shorter than 0.8λ and/or longer than 1.2λ after the pulsed light exits from the article (ex: polarizer). In one embodiment, the filter means 406 filters out light having wavelengths shorter than 0.9λ and/or longer than 1.1λ after the pulsed light exits from the article. In one embodiment, the filter means 406 filters out light having wavelengths substantially shorter and/or longer than λ after the pulsed light exits from the article. Accordingly, besides one color filter, two or more color filters can be adopted in the apparatus of multi-photon fluorescence microscope of the embodiment for filtering out light with wavelengths other than the wavelength of the to-be-analyzed output light.

Also, the apparatus of multi-photon fluorescence microscope of the embodiment may further include mirror means such as the first mirror $M_1$ and the second mirror $M_2$ for directing the coherent pulsed light along an optical path, wherein the first mirror $M_1$ directs the coherent pulsed light to the lens means 403 to cause the coherent pulsed light to impinge on the target material at the article; and the second mirror $M_2$ directs the pulsed light exiting from the article to the detector 405. Moreover, the detector 405 can be further linked to a lock-in amplifier 408 to increase the signal to noise ratio.

Figure 5:
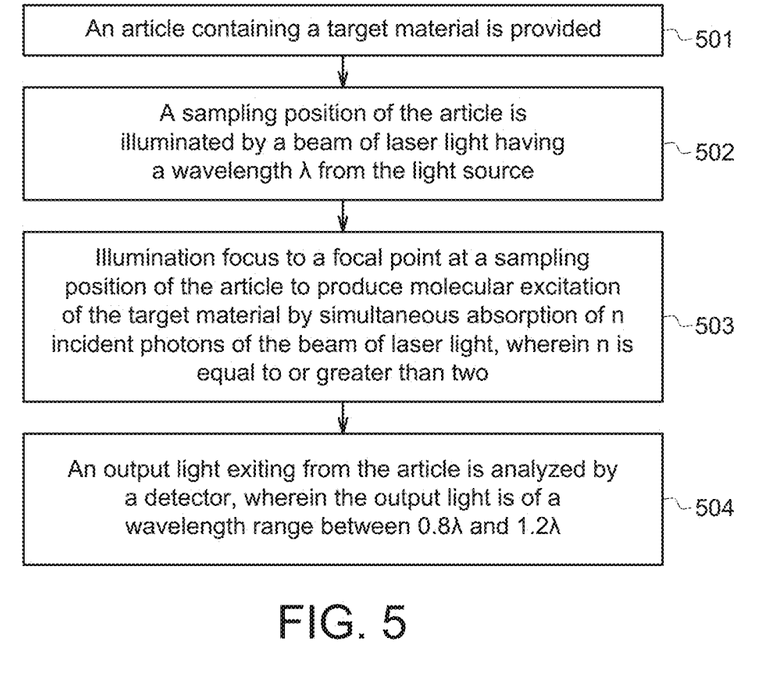
FIG. 5 is a flow of a method for inspecting an article according to one embodiment of the disclosure.

FIG. 5 is a flow of a method for inspecting an article according to one embodiment of the disclosure. According to an embodiment, in step 501, an article containing a target material (such as a polarizer having a PVA layer containing iodine-dyed ions) is provided. In step 502, a sampling position of the article is illuminated by a beam of laser light having a wavelength λ from the light source 402. In step 503, illumination focus to a focal point at a sampling position of the article to produce molecular excitation of the target material by simultaneous absorption of n incident photons of the beam of laser light, wherein n is equal to or greater than two. Then, in step 504, an output light exiting from the article is analyzed by a detector, wherein the output light is of a wavelength range between 0.8λ and 1.2λ. For example, after the beam of laser light exits from the article (such as optical matter), an output light intensity at the wavelength λ is detected by the detector 405, so as to obtain an intensity loss of the pumped incident photons of the wavelength λ. In one embodiment, the beam of laser light has the wavelength λ longer than about 900 nm. In some embodiments, the beam of laser light has the wavelength λ in a range of longer than about 900 nm and shorter than about 1600 nm. In some embodiments, the beam of laser light has the wavelength λ in a range of longer than about 900 nm and shorter than about 1200 nm. Also, the method for inspecting an article according to one embodiment may further include the step of filtering out light having wavelengths other than a range of 0.8λ to 1.2λ by the filter means 406 (shown in FIG. 4, and the filter means 406 including such as one or more optical filters) after the beam of laser light exits from the article; for example, filtering out light having wavelengths substantially other than λ.

In the embodiment, it is assumed that a surface of the article (ex: polarizer) on the stage means 401 is parallel to a xy-plane, and the method comprise scanning through the article at the sampling position in a z-direction vertical to the xy-plane, and each scan comprises the aforementioned step 502 (illuminating step), step 503 (focusing step) and step 504 (analyzing step), so as to obtain an axial distribution along the z-direction of the target material (ex: iodine-dyed ions) inside the article (ex: polarizer) in a non-invasive way.

Moreover, for a to-be-detected article, several sampling positions can be selected for performing the inspection if necessary. Thus, the method for inspecting an article according to one embodiment may further include the step of selecting other sampling position(s); repeating the illuminating, focusing and analyzing steps as described above at the selected other sampling position(s); and scanning the article at other sampling position(s) in the z-direction.

In the following descriptions, one of the experimental setups, including related components of the apparatus using a m-TPF of the embodiment, and the experimental results are provided for the illustration. However, those numerical values and specifications of the related components and results are only provided for illustration, not for limitation.

<Experiments and Results>

As shown in FIG. 4, the source 402 for one embodied m-TPF microscope in the experiment is a compact Ytterbium laser with a 250 femtosecond output pulse duration and 1.03 μm (1030 nm) central wavelength, and an isolator ISO is incorporated in the embodied m-TPF microscope. The polarization of the output laser beam from the source 402 is transformed into circular polarization by a quarter-wave plate. A pair of lenses $L_1$ and $L_2$ is adopted for beam expansion so that the full aperture focusing objective $OBJ_1$ is utilized to maximize the spatial resolution in the lateral (x and y) and the axial direction (z-direction). The focusing objective $OBJ_1$ had a 0.75 numerical aperture (NA). The residual pumped incident photons (central wavelength of 1030 nm) is then collected by another condenser $OBJ_2$ with a 0.90 NA and focused into an unamplified detector 405 (DET 36A, Thorlabs). The average power of the sample is decayed to 1 mW to avoid the photo-bleach and photo-damage of the iodine-dyed PVA polymer films. One long-pass color-glass filter (RG-850; i.e. filter means 406), is placed before the detector 405 to block out possible unwanted visible wavelength noise from the background. By scanning the relative positions between the focusing objective $OBJ_1$ and polarizer, the axial distribution of Iodine-ion-concentration in the PVA film was sequentially measured. From the basic Gaussian beam optics and experimental parameters, the calculated diffraction-limited spot size ($2\omega_0$), and the corresponding confocal depth, b, were 1.65 μm and 6.22 μm, respectively.

In the two-photon microscope, since the intensities of TPF or TPA are equal to the intensity square of the fundamental 1.03 μm pumped Gaussian beam, the spatial resolutions in the x, y, and z directions are smaller than those in traditional microscopes. The spatial resolutions in the x and y directions of the modified TPF microscope are 0.57 μm, which are equal to $\omega_0$ divided by $\sqrt{2}$. On the other hand, the spatial resolution in the z-direction, defined as the full-width-half-maximum of the TPF or TPA intensity, is equal to 0.643 b. In this exemplified experiment, the axial resolution is 4.13 μm.

Since the axial distributions of iodine-doped ion distributions are related to the durability of the polarizer, measuring the doped Iodine distributions in the depth direction (z-direction) in real time is very helpful for understanding the polarizer properties. In a durable polarizer, the iodine ions are nearly equally dispersed within the PVA layer. In contrast, in a poorly-durable polarizer, the doped iodine ions within the PVA layer may aggregate in the interface between the PVA layer and TAC layer. The clustered iodine-ions diffuse easily to the TAC layer over time and thus the polarization properties can easily vanish, thereby leading to degradation of the contrast ratio and hue balance in liquid-crystal displays. Accordingly, it is important to measure the depth-dependent iodine traces during the fabrication process of the polarizer in real time. If any unusual axial Iodine distribution is observed, the fabrication process could be terminated or modified in time to save the cost and time.

Figure 6A:
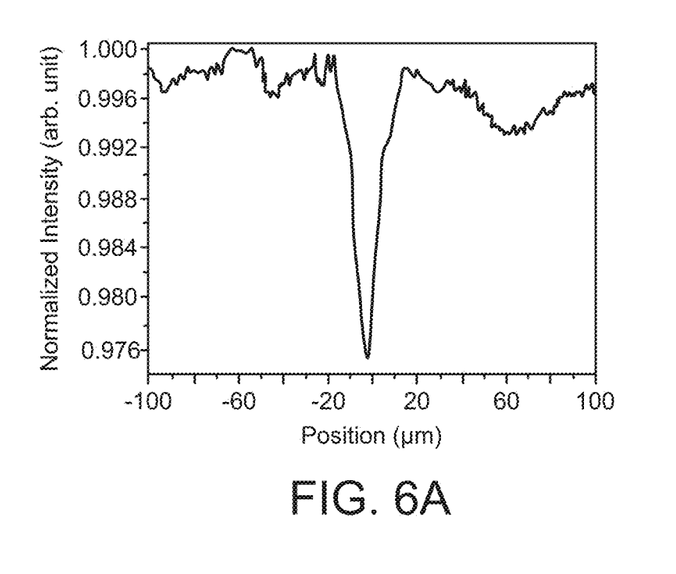
FIG. 6A and FIG. 6B show experimental results of the depth scanning traces of the durable and poorly-durable polarizers obtained with the m-TPF microscope of an embodiment, respectively.
Figure 6B:
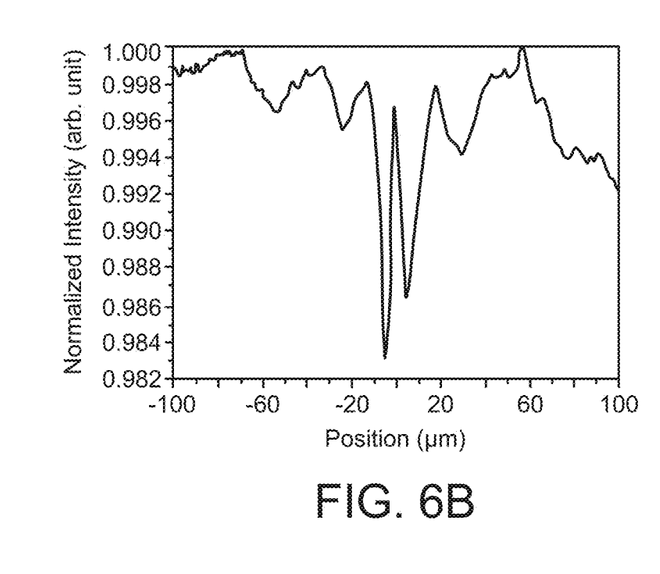

FIG. 6A and FIG. 6B show experimental results of the depth (i.e. along the z-direction) scanning traces of the durable and poorly-durable polarizers obtained with the m-TPF microscope of an embodiment, respectively. In the experiments, the z-step size is 1 μm. Based on the depth-dependent loss of the pumping photon intensity along the scanning trace, the relative axial distribution of iodine-dyed ions can be monitored and the durability of the polarizer can thus be predicted prior to packaging in a fast and noninvasively way. FIG. 6A and FIG. 6B show the maximum decrease of intensity in the residual pumped incident photons, which was 2.5% and 1.7% in the durable and poorly-durable iodine-dyed polarizers, respectively, that occurs due to the strong TPA effects in the iodine-molecules. The measured width of iodine-dyed layers, defined by the start point and the end point of the TPA effect during the scanning process, is 31 μm in both of FIG. 6A and FIG. 6B, which is in good agreement with a thickness of 25 μm for the iodine-dyed layer and the calculated 4.1 μm axial resolution of the m-TPF microscope. The acquisition time for one depth-dependent pump intensity loss is about 1 minute, and is limited by the integration time of the lock-in amplifier 408 (SR830, Stanford Research System) and the processing time of the controlling software (Labview 2010, National Instruments).

As can be seen from the measured z-traces in FIG. 6A and FIG. 6B, the method of the embodiment provides an efficient and effective way to monitor quality of the polarizers during the ion-doping process without the necessity of physical sampling, which is a destructive and very time-consuming process. Furthermore, a modified multi-photon fluorescence microscope such as an m-TPF microscope described in the embodiment has the potential to be applied for noninvasively monitoring or predicting the optical quality of doped-ion-based optical elements, such as laser crystals and OLED-based lighting devices.

Figure 7A:
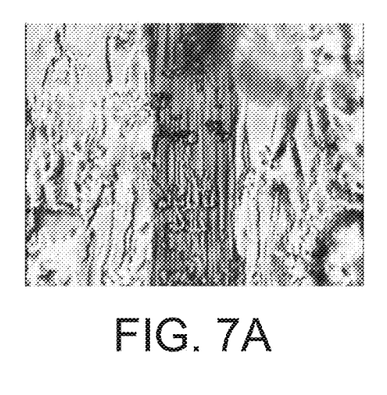
FIG. 7A and FIG. 7B show the microscope images of the durable and poorly-durable polarizers where the PVA layers are included.
Figure 7B:
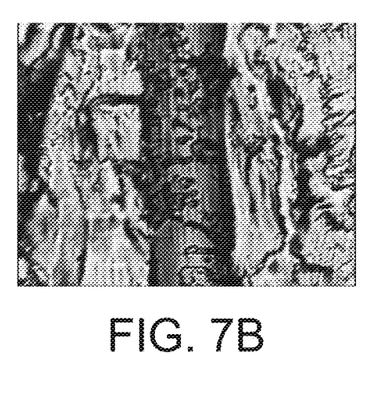
Figure 7C:
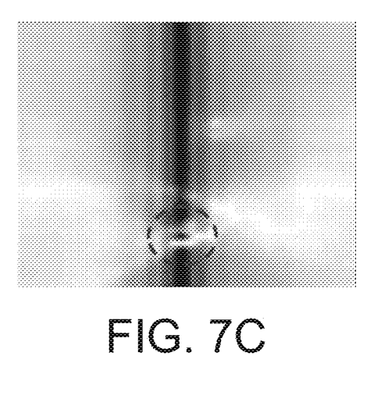
FIG. 7C shows two-dimensional (2D) virtual biopsy images of a polarizer in the x-z plane obtained with the m-TPF microscope of an embodiment.

Although the z-dependent traces are enough to measure the durability of the polarizer, the image-level comparisons are also conducted in the experiment. FIG. 7A and FIG. 7B show the microscope images of the durable and poorly-durable polarizers where the PVA layers are included. FIG. 7C shows 2D virtual biopsy images of a polarizer in the x-z plane obtained by reconstruction of the article from TPA effects detected at different focal planes with the m-TPF microscope of an embodiment. All the image sizes in FIG. 7A to FIG. 7C are 100 μm by 100 μm. The PVA layers are vertically located in the center of the three images in FIG. 7A to FIG. 7C with a thickness of 25 μm.

As performed in the conventional inspecting way, the invasive and time-consuming sample preparation procedures are required for obtaining the microscopic images such as those in FIG. 7A and FIG. 7B, which include the removal, slicing, fixation, and observation of iodine-dyed distribution in the PVA film under the microscope, cannot be easily executed without professional skills and special slicing machines. FIG. 7A shows a microscopic image of the iodine-dopants in a durable polarizer equally dispersed within the PVA layer. In contrast, in FIG. 7B, in the poorly durable polarizer, the doped iodine ions have aggregated in the interfaces between the PVA layer and TAC layer. In addition to the time-consuming process, the contrasts in traditional microscopic images are relatively small, so that skilled operators are needed for the image determination for durable and poorly-durable films. However, the inspecting method and the modified laser scanning microscope of the embodiment solve those problems. FIG. 7C shows the virtual biopsy images of a polarizer film in the X-Z direction taken by the m-TPF microscope of an embodiment. The images are directly recorded and linearly re-scaled with a computer. In FIG. 7C, the distributions of iodine-ions can be easily distinguished. In this demonstration case, most parts in the PVA layer are seen to be durable, since the iodine-ions are uniformly distributed throughout the whole PVA layer. In the image near the bottom of FIG. 7C, a small portion of the PVA layer (enclosed in the dashed circle) can be seen where the iodine-ions are not equally dispersed within the PVA layer. If those defects are not detected and the fabrication process is not terminated in time, there is a higher chance to form white or black spots in the liquid crystal displays applied with the polarizer with those defects.

According to the aforementioned descriptions, a novel method for inspecting an article and an apparatus of modified multi-photon fluorescence microscope for tracing the target material in the article (ex: ion-distribution deep inside an optical matter) are disclosed. As illustrated in the demonstrating example for observing the iodine-ion concentration in PVA layer deep within the polarizer, the 1D and 2D spatial distributions of iodine-dyed ions can be successfully measured by the multi-photon fluorescence microscope in a fast and non-invasive way. The experimental results clearly show that the quality of polarizer can be quickly distinguished from the 1D axial distributions of Iodine-dyed ions observed through the non-biopsy method of the embodiment. The demonstrated experimental results show great potential for monitoring the spatial distributions of the target material in the article (ex: doped-ions in an optical matter) in a non-time-consuming, fast, and non-destructive way, which will benefit both scientific researches by allowing more information about spatial distributions of doped ions to be known and industrial applications by finding problems during the fabrication process of these optical elements.

Other embodiments with different arrangement and setup of the related components of the multi-photon fluorescence microscope may also be applicable and could be varied depending on the actual needs of the applications. It is, of course, noted that the configurations of FIG. 4 is depicted only for demonstration, not for limitation. It is known by people skilled in the art that the number of photon absorption (ex: two, three or more) by the target material, the numerical values of apertures of objectives, the thickness of the related layers, spatial resolution, axial resolution, etc., are not limited by the description provided herein, and could be adjusted and modified according to the requirements and/or fabrication in the practical applications.

While the disclosure has been described by way of example and in terms of the exemplary embodiment(s), it is to be understood that the disclosure is not limited thereto. On the contrary, it is intended to cover various modifications and similar arrangements and procedures, and the scope of the appended claims therefore should be accorded the broadest interpretation so as to encompass all such modifications and similar arrangements and procedures.

What is claimed is:

1. A method for inspecting an article, comprising:
providing the article containing a target material;
illuminating a sampling position of the article by a beam of laser light having a wavelength $\lambda$;
focusing said illumination to a focal point at the sampling position of the article to produce molecular excitation of the target material by simultaneous absorption of n incident photons of the beam of laser light, wherein n is equal to or greater than two; and
analyzing an output light exiting from the article by a detector, comprises:
detecting a light intensity of the output light by the detector, so as to obtain an intensity loss of the incident photons of the beam of laser light of the wavelength range between $0.8\lambda$ and $1.2\lambda$, wherein the intensity loss results from a multi-photon absorption effect.

2. The method according to claim 1, wherein the beam of laser light has the wavelength $\lambda$ longer than about 900 nm.

3. The method according to claim 1, wherein the beam of laser light has the wavelength $\lambda$ in a range of longer than about 900 nm and shorter than about 1600 nm.

4. The method according to claim 1, wherein the beam of laser light has the wavelength $\lambda$ in a range of longer than about 900 nm and shorter than about 1200 nm.

5. The method according to claim 1, further comprising:
filtering out light having wavelengths shorter than $0.8\lambda$ or longer than $1.2\lambda$ by an optical filter before said analyzing, or filtering out light having wavelengths shorter than $0.8\lambda$ and longer than $1.2\lambda$ by at least two of the optical filters before said analyzing.

6. The method according to claim 1, further comprising:
filtering out light having wavelengths shorter than $\lambda$ or longer than $\lambda$ by an optical filter after the beam of laser light exiting from the article, or filtering out light having wavelengths shorter than $\lambda$ and longer than $\lambda$ by at least two of the optical filters.

7. The method according to claim 1, wherein a surface of the article is parallel to a xy-plane, and the method comprise:
scanning through the article at the sampling position in a z-direction vertical to the xy-plane, and each scan comprises said illuminating, focusing and analyzing steps.

8. The method according to claim 1, wherein the method is applied to detect an ion concentration distribution of the target material.

9. The method according to claim 1, wherein n is equal to two.

10. The method according to claim 1, wherein the article is a polarizing plate and the target material is doped iodine ions.

11. An apparatus for measuring an article by a multi-photon excitation technique, at least comprising:
stage means for receiving the article containing a target material;
at least one source of coherent pulsed light having a wavelength $\lambda$;
lens means for focusing the coherent pulsed light to an object plane within the article at a sampling position, thereby causing the target material to simultaneously absorb n photons of the coherent pulsed light, wherein n is equal to or greater than two; and
a detector for detecting a light intensity of an output light exiting from the article, so as to obtain an intensity loss of the photons of the coherent pulsed light of the wavelength range between 0.8λ and 1.2λ, wherein the output light has a wavelength range between 0.8λ and 1.2λ, and the intensity loss results from a multi-photon absorption effect.

12. The apparatus according to claim 11, wherein the at least one source of the coherent pulsed light has the wavelength λ longer than about 900 nm.

13. The apparatus according to claim 11, wherein the at least one source of the coherent pulsed light has the wavelength λ in a range of longer than about 900 nm and shorter than about 1600 nm.

14. The apparatus according to claim 11, wherein the at least one source of the coherent pulsed light has the wavelength λ in a range of longer than about 900 nm and shorter than about 1200 nm.

15. The apparatus according to claim 11, further comprising:
   a filter means for filtering out light having wavelengths shorter than 0.8λ or longer than 1.2λ after the coherent pulsed light exiting from the article.

16. The apparatus according to claim 11, wherein the apparatus is configured to detect an ion concentration distribution of the target material.

17. The apparatus according to claim 11, wherein a surface of the article is parallel to a xy-plane, and the stage means comprise a moveable stage which enables the article to be scanned at the sampling position in a z-direction vertical to the xy-plane.

18. The apparatus according to claim 11, further comprising mirror means for directing the coherent pulsed light along an optical path, and the mirror means comprising:
   a first mirror for directing the coherent pulsed light to the lens means to cause the coherent pulsed light to impinge on the target material at the object plane; and
   a second mirror for directing the coherent pulsed light exiting from the article to the detector.

19. The apparatus according to claim 11, wherein n is equal to two.

20. The apparatus according to claim 11, wherein the article is a polarizing plate and the target material is doped iodine ions.

* * * * *